(12) United States Patent
Song et al.

(10) Patent No.: US 11,662,662 B2
(45) Date of Patent: May 30, 2023

(54) PHOTO-DECOMPOSABLE COMPOUND, PHOTORESIST COMPOSITION INCLUDING THE SAME, AND METHOD OF MANUFACTURING INTEGRATED CIRCUIT DEVICE

(71) Applicant: SAMSUNG ELECTRONICS CO., LTD., Suwon-si (KR)

(72) Inventors: Hyunji Song, Anyang-si (KR); Sukkoo Hong, Suwon-si (KR); Sumin Kim, Suwon-si (KR); Yechan Kim, Suwon-si (KR); Juyoung Kim, Usan (KR); Jinjoo Kim, Seoul (KR); Hyunwoo Kim, Seongnam-si (KR); Juhyeon Park, Suwon-si (KR); Songse Yi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 210 days.

(21) Appl. No.: 16/994,957

(22) Filed: Aug. 17, 2020

(65) Prior Publication Data

US 2021/0223692 A1 Jul. 22, 2021

(30) Foreign Application Priority Data

Jan. 20, 2020 (KR) .................... 10-2020-0007385

(51) Int. Cl.
| | | |
|---|---|---|
| G03F 7/004 | (2006.01) | |
| G03F 7/039 | (2006.01) | |
| C07D 213/68 | (2006.01) | |
| C07D 263/32 | (2006.01) | |
| C07D 233/64 | (2006.01) | |
| C07D 277/26 | (2006.01) | |

(52) U.S. Cl.
CPC ......... *G03F 7/0045* (2013.01); *C07D 213/68* (2013.01); *C07D 233/64* (2013.01); *C07D 263/32* (2013.01); *C07D 277/26* (2013.01); *G03F 7/0392* (2013.01)

(58) Field of Classification Search
None
See application file for complete search history.

(56) References Cited

U.S. PATENT DOCUMENTS

| | | | | |
|---|---|---|---|---|
| 8,460,851 B2 * | 6/2013 | Yamaguchi | ........... | G03F 7/0397 548/215 |
| 8,574,812 B2 * | 11/2013 | Ichikawa | .............. | G03F 7/0397 430/920 |
| 8,663,899 B2 * | 3/2014 | Ichikawa | .............. | G03F 7/0045 430/920 |
| 8,703,404 B2 | 4/2014 | Hatakeyama et al. | | |
| 8,715,903 B2 * | 5/2014 | Tomeba | ................ | G03F 7/0046 430/913 |
| 8,735,047 B2 * | 5/2014 | Ichikawa | .............. | G03F 7/0397 430/311 |
| 8,852,846 B2 * | 10/2014 | Anryu | ................... | G03F 7/0046 430/326 |
| 8,921,028 B2 * | 12/2014 | Yamaguchi | ........... | G03F 7/0045 430/920 |
| 8,940,476 B2 * | 1/2015 | Yamaguchi | ............. | G03F 7/325 430/287.1 |
| 9,040,224 B2 | 5/2015 | Kawaue et al. | | |
| 9,176,378 B2 * | 11/2015 | Ichikawa | .............. | G03F 7/0397 |
| 9,213,234 B2 | 12/2015 | Chang | | |
| 9,405,187 B2 * | 8/2016 | Hiraoka | ............... | C07D 207/12 |
| 9,507,259 B2 | 11/2016 | Li et al. | | |
| 9,551,930 B2 | 1/2017 | LaBeaume et al. | | |
| 9,581,908 B2 | 2/2017 | Wu et al. | | |
| 9,760,003 B2 * | 9/2017 | Iwato | ........................ | G03F 7/40 |
| 9,851,636 B2 * | 12/2017 | Liu | ....................... | G03F 7/0392 |

(Continued)

FOREIGN PATENT DOCUMENTS

| | | | | |
|---|---|---|---|---|
| EP | 2372455 A2 | 5/2011 | | |
| KR | 2011073300 A * | 6/2011 | ........... | C07C 381/12 |

(Continued)

OTHER PUBLICATIONS

International Union of Pure and Applied Chemistry, Compendium of Chemical Terminology (IUPAC), Gold Book, p. 1474 of 1622 (2012) ("Gold Book") (Year: 2012).*

(Continued)

*Primary Examiner* — Alexander R Pagano
(74) *Attorney, Agent, or Firm* — Lee IP Law, P.C.

(57) ABSTRACT

A photo-decomposable compound, a photoresist composition, and a method of manufacturing an IC device, the compound generating acid upon exposure and acts as a quenching base that neutralizes acid in an unexposed state and being represented by Formula 1:

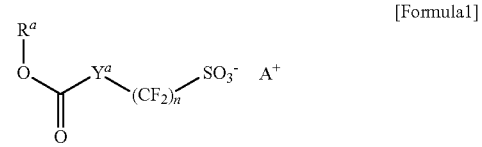

[Formula 1]

wherein, in Formula 1, $R^a$ is a C5 to C40 substituted or unsubstituted cyclic hydrocarbon group including at least one nitrogen atom, $Y^a$ is a C1 to C20 divalent linear or cyclic hydrocarbon group, n is an integer of 1 to 5, and $A^+$ is a counter ion.

14 Claims, 5 Drawing Sheets

(56) References Cited

U.S. PATENT DOCUMENTS

| | | | |
|---|---|---|---|
| 10,042,251 B2 | 8/2018 | LaBeaume et al. | |
| 10,048,594 B2 | 8/2018 | Carcasi et al. | |
| 2011/0318688 A1* | 12/2011 | Hiraoka | C07D 207/12 |
| | | | 549/16 |
| 2015/0346599 A1 | 12/2015 | LaBeaume | |
| 2015/0370164 A1 | 12/2015 | Chen | |

FOREIGN PATENT DOCUMENTS

| | | | | |
|---|---|---|---|---|
| KR | 2011093655 A | * | 8/2011 | ........... C07D 277/34 |
| KR | 10-2014-0029704 A | | 3/2014 | |

OTHER PUBLICATIONS

J. Brecher, Graphical Representation Standards for Chemical Structure Diagrams (IUPAC Recommendations 2008), 80 Pure Appl. Chem. 277-410 (2008) (Year: 2008).*

* cited by examiner

PHOTO-DECOMPOSABLE COMPOUND, PHOTORESIST COMPOSITION INCLUDING THE SAME, AND METHOD OF MANUFACTURING INTEGRATED CIRCUIT DEVICE

CROSS-REFERENCE TO RELATED APPLICATION

Korean Patent Application No. 10-2020-0007385, filed on Jan. 20, 2020, in the Korean Intellectual Property Office, and entitled: "Photo-Decomposable Compound, Photoresist Composition Including the Same, and Method of Manufacturing Integrated Circuit Device," is incorporated by reference herein in its entirety.

BACKGROUND

1. Field

Embodiments relate to a photo-decomposable compound, a photoresist composition including the same, and a method of manufacturing an integrated circuit (IC) device.

2. Description of the Related Art

As IC devices have rapidly been downscaled and highly integrated, there is a new technique for ensuring the dimensional precision of a pattern to be formed when the pattern is formed using a photolithography process.

SUMMARY

The embodiments may be realized by providing a photo-decomposable compound, which generates acid upon exposure and acts as a quenching base that neutralizes acid in an unexposed state, the photo-decomposable compound being represented by Formula 1:

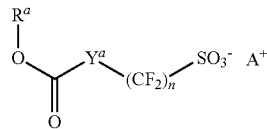

[Formula 1]

wherein, in Formula 1, $R^a$ is a C5 to C40 substituted or unsubstituted cyclic hydrocarbon group including at least one nitrogen atom, $Y^a$ is a C1 to C20 divalent linear or cyclic hydrocarbon group, n is an integer of 1 to 5, and $A^+$ is a counter ion.

The embodiments may be realized by providing a photoresist composition including a chemically amplified polymer; a photoacid generator (PAG); a photo-decomposable compound that generates acid upon exposure and acts as a quenching base that neutralizes acid in an unexposed state; and a solvent, wherein the photo-decomposable compound is represented by Formula 1:

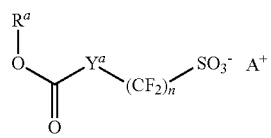

[Formula 1]

wherein, in Formula 1, $R^a$ is a C5 to C40 substituted or unsubstituted cyclic hydrocarbon group including at least one nitrogen atom, $Y^a$ is a C1 to C20 divalent linear or cyclic hydrocarbon group, n is an integer of 1 to 5, and $A^+$ is a counter ion.

The embodiments may be realized by providing a method of manufacturing an integrated circuit (IC) device, the method including providing a substrate that includes a feature layer; forming a photoresist film on the feature layer, the photoresist film including a chemically amplified polymer, a photoacid generator (PAG), and a photo-decomposable compound represented by Formula 1; exposing a first area of the photoresist film to generate a first acid and a second acid in the first area of the photoresist film, wherein the first area is a portion of the photoresist film, the first acid is derived from the PAG, and the second acid is derived from the photo-decomposable compound; deprotecting an acid-labile group included in the chemically amplified polymer by using the first acid and the second acid in the exposed first area of the photoresist film; removing the exposed first area of the photoresist film by using a developer to form a photoresist pattern comprising a non-exposed area of the photoresist film; and processing the feature layer using the photoresist pattern,

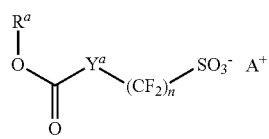

[Formula 1]

wherein, in Formula 1, $R^a$ is a C5 to C40 substituted or unsubstituted cyclic hydrocarbon group including at least one nitrogen atom, $Y^a$ is a C1 to C20 divalent linear or cyclic hydrocarbon group, n is an integer of 1 to 5, and $A^+$ is a counter ion.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
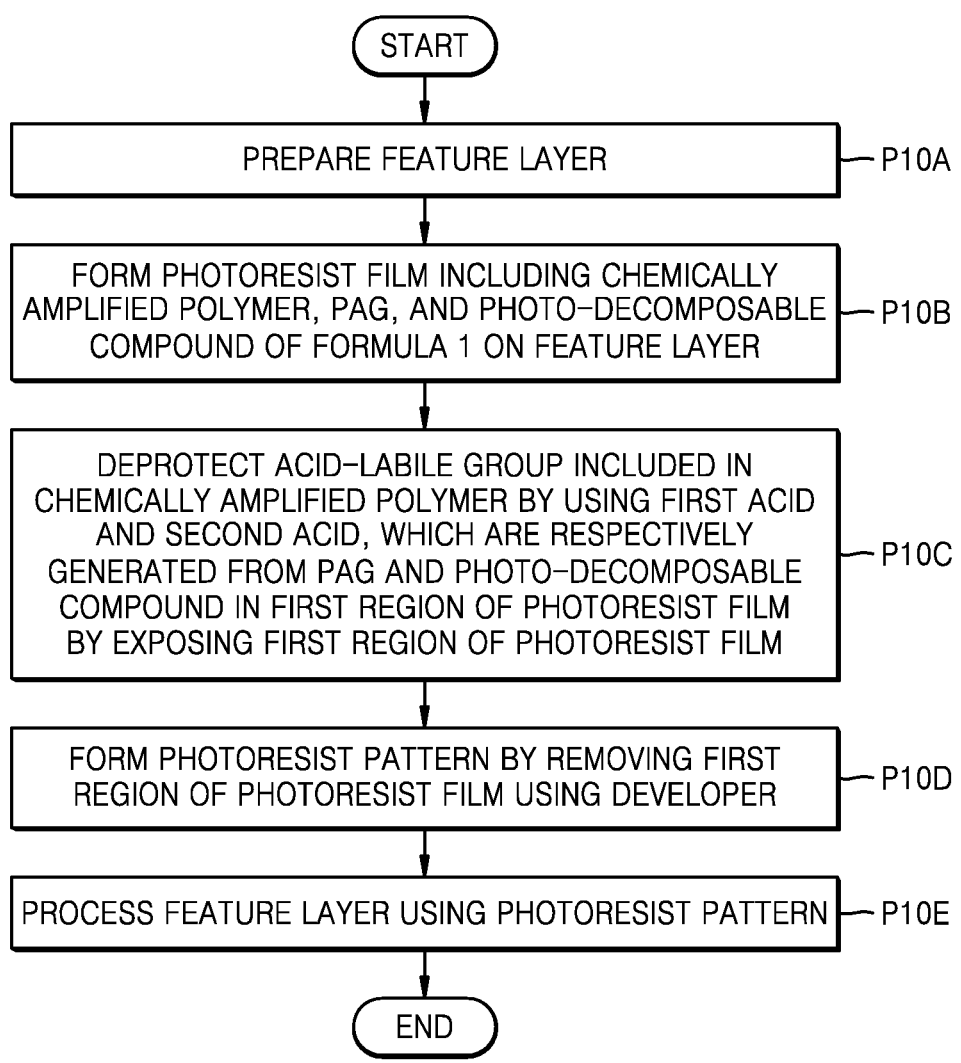
FIG. 1 is a flowchart of a method of manufacturing an integrated circuit (IC) device, according to embodiments.

A photo-decomposable compound according to embodiments may generate acid upon exposure and act as a quenching base that neutralizes acid before exposure or in an unexposed state. The photo-decomposable compound according to the embodiments may be represented by Formula 1.

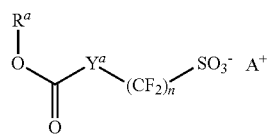

[Formula 1]

In Formula 1, $R^a$ may be, e.g., a C5 to C40 substituted or unsubstituted cyclic hydrocarbon group including at least one heteroatom. In an implementation, the heteroatom may be, e.g., a nitrogen atom.

$Y^a$ may be, e.g., a C1 to C20 divalent linear or cyclic hydrocarbon group.

n may be, e.g., an integer of 1 to 5.

$A^+$ may be a counter ion.

As used herein, the term "substituted" may refer to including at least one substituent. The substituent may include a halogen atom selected from fluorine (F), chlorine (Cl), bromine (Br), and iodine (I), hydroxyl, amino, thiol, carboxyl, carboxylate, ester, amide, nitrile, sulfide, disulfide, nitro, C1-C20 alkyl, C1-C20 cycloalkyl, C2-C20 alkenyl, C1-C20 alkoxy, C2-C20 alkenoxy, C6-C30 aryl, C6-C30 aryloxy, C7-C30 alkylaryl, or C7-C30 alkylaryloxy.

The photo-decomposable compound may generate acid when exposed to active radiation, e.g., a krypton fluoride (KrF) excimer laser (248 nm), an argon fluoride (ArF) excimer laser (193 nm), a fluorine ($F_2$) excimer laser (157 nm), or an extreme ultraviolet (EUV) laser (13.5 nm).

In an implementation, in Formula 1, $R^a$ may be a monocyclic aromatic hydrocarbon group including a nitrogen atom as the heteroatom. In an implementation, $R^a$ may be, e.g., one of the following groups, in which "*" indicates a bonding site.

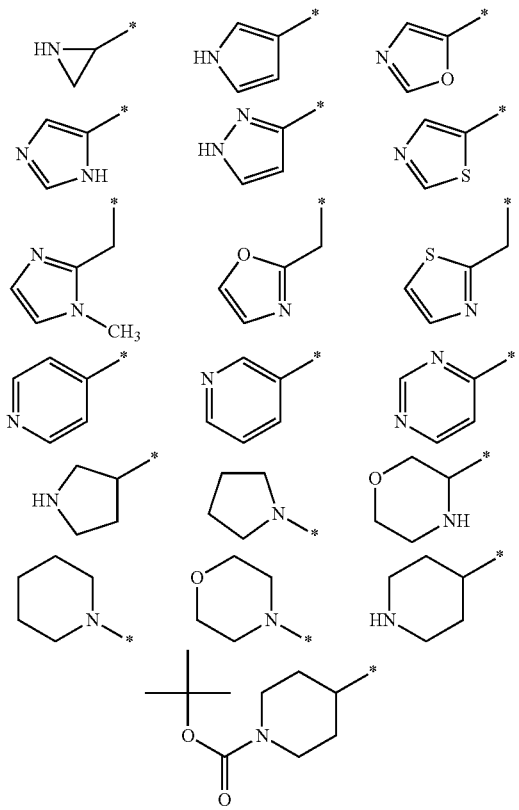

In an implementation, in Formula 1, $R^a$ may be a condensed aromatic hydrocarbon group including a nitrogen atom as the heteroatom. In an implementation, $R^a$ may be, e.g., one of the following groups, in which "*" indicates a bonding site.

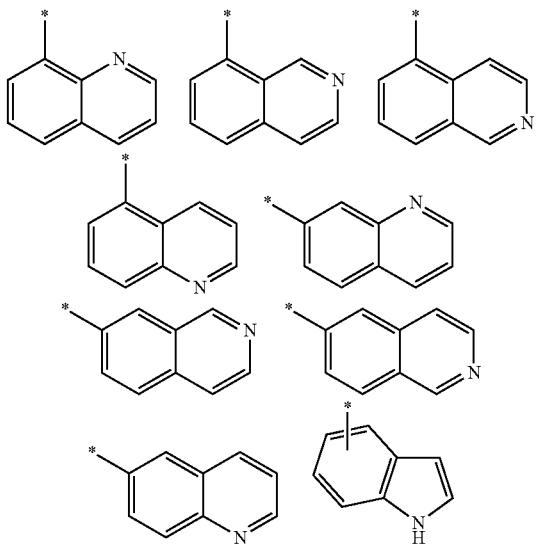

In Formula 1, $Y^a$ may be, e.g., a C1 to C5 substituted or unsubstituted alkylene group, a C5 to C20 divalent monocyclic or condensed alicyclic hydrocarbon group, or a C5 to C20 divalent monocyclic or condensed aromatic hydrocarbon group.

In an implementation, $Y^a$ may be, e.g., $-(CH_2)_m-$ (in which m may be, e.g., an integer of 1 to 5).

In an implementation, $Y^a$ may be, e.g., one of the following divalent groups.

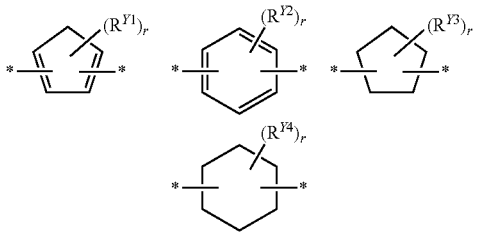

"*" indicates a bonding site, r may be, e.g., an integer of 0 to 2, and each of $R^{Y1}$, $R^{Y2}$, $R^{Y3}$, and $R^{Y4}$ may independently be, e.g., a C1 to C10 (e.g., linear or branched) alkyl group, a cyclopropyl group, a cyclopentyl group, or a cyclohexyl group.

In an implementation, in Formula 1, $A^+$ may be, e.g., a sulfonium cation, an iodonium cation, or an ammonium cation. In an implementation, $A^+$ may include, e.g., a sulfonium cation represented by Formula 2, an iodonium cation represented by Formula 3, or an ammonium cation represented by Formula 4.

[Formula 2]

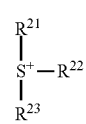

[Formula 3]

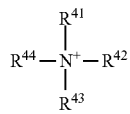

[Formula 4]

In Formulae 2 to 4, each of $R^{21}$, $R^{22}$, $R^{23}$, $R^{31}$, $R^{32}$, $R^{41}$, $R^{42}$, and $R^{43}$ may independently be, e.g., a C1-C30 hydrocarbon group, which may include a heteroatom, and $R^{44}$ may be a C1-C30 hydrocarbon group, which may include a heteroatom, or a hydrogen atom. In an implementation, two of $R^{21}$, $R^{22}$, and $R^{23}$ may be bonded together to form a ring with a sulfur atom to which the two selected ones are bonded. In an implementation, two of $R^{41}$, $R^{42}$, $R^{43}$, and $R^{44}$ may be bonded together to form a ring with a nitrogen atom to which the two selected ones are bonded.

In an implementation, each of the hydrocarbon groups included in $R^{21}$, $R^{22}$, $R^{23}$, $R^{31}$, $R^{32}$, $R^{41}$, $R^{42}$, $R^{43}$, and $R^{44}$ may be a linear, branched, or cyclic hydrocarbon group. In an implementation, the hydrocarbon group may include an alkyl group, such as methyl, ethyl, n-propyl, isopropyl, n-butyl, and t-butyl; a monovalent saturated cycloaliphatic hydrocarbon group, such as cyclopropyl, cyclopentyl, cyclohexyl, cyclopropylmethyl, 4-methylcyclohexyl, cyclohexylmethyl, norbornyl, and adamantyl; an alkenyl group, such as vinyl, allyl, prophenyl, butenyl, and hexenyl; a monovalent unsaturated cycloaliphatic hydrocarbon group, such as cyclohexenyl; an aryl group, such as phenyl and naphthyl; a heteroaryl group, such as thienyl; or an aralkyl group, such as benzyl, 1-phenylethyl, and 2-phenylethyl.

In an implementation, in $R^{21}$, $R^{22}$, $R^{23}$, $R^{31}$, $R^{32}$, $R^{41}$, $R^{42}$, $R^{43}$, and $R^{44}$, some of hydrogen atoms may be substituted or replaced with a heteroatom-containing group, such as oxygen, sulfur, nitrogen, or a halogen, and some of carbon atoms may be substituted or replaced with a heteroatom-containing group, such as oxygen, sulfur, or nitrogen. Each of $R^{21}$, $R^{22}$, $R^{23}$, $R^{31}$, $R^{32}$, $R^{41}$, $R^{42}$, $R^{43}$, and $R^{44}$ may independently include, e.g., a hydroxyl moiety, a cyano moiety, a carbonyl moiety, an ether bond, an ester bond, a sulfonic acid ester bond, a carbonate bond, a lactone ring, a sultone ring, carboxylic anhydride, or a haloalkyl moiety.

In an implementation, the sulfonium cation represented by Formula 2 may include, e.g., one of the following ions.

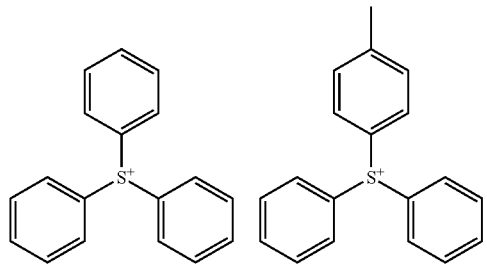

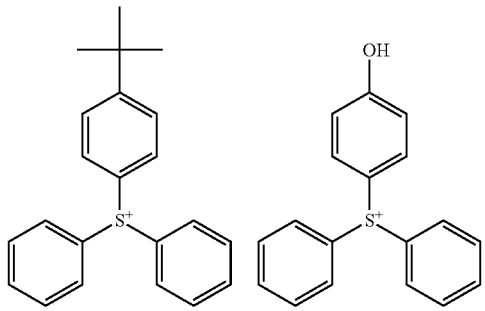

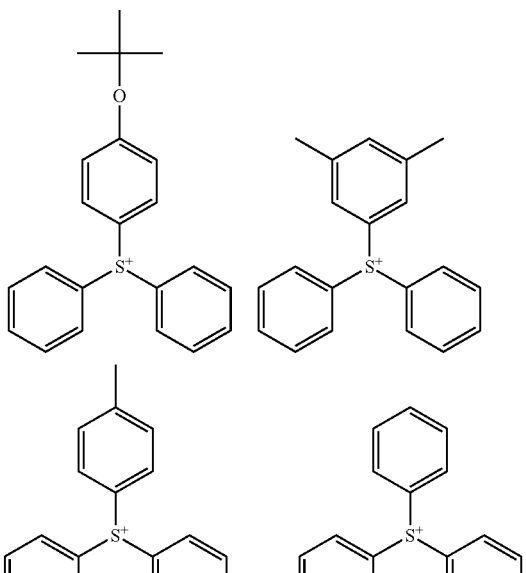

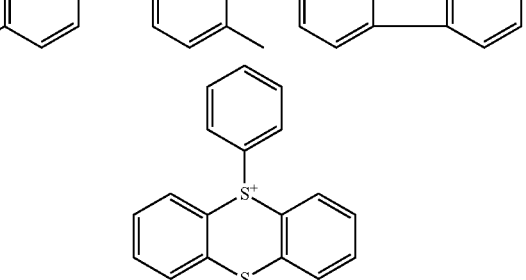

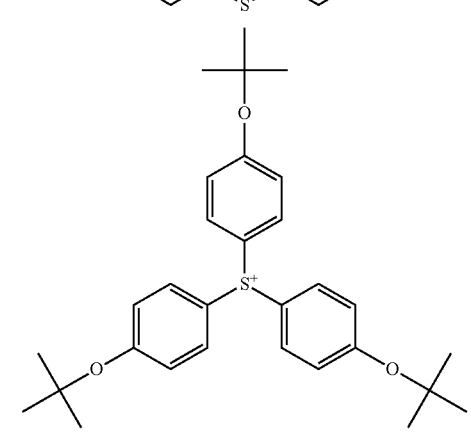

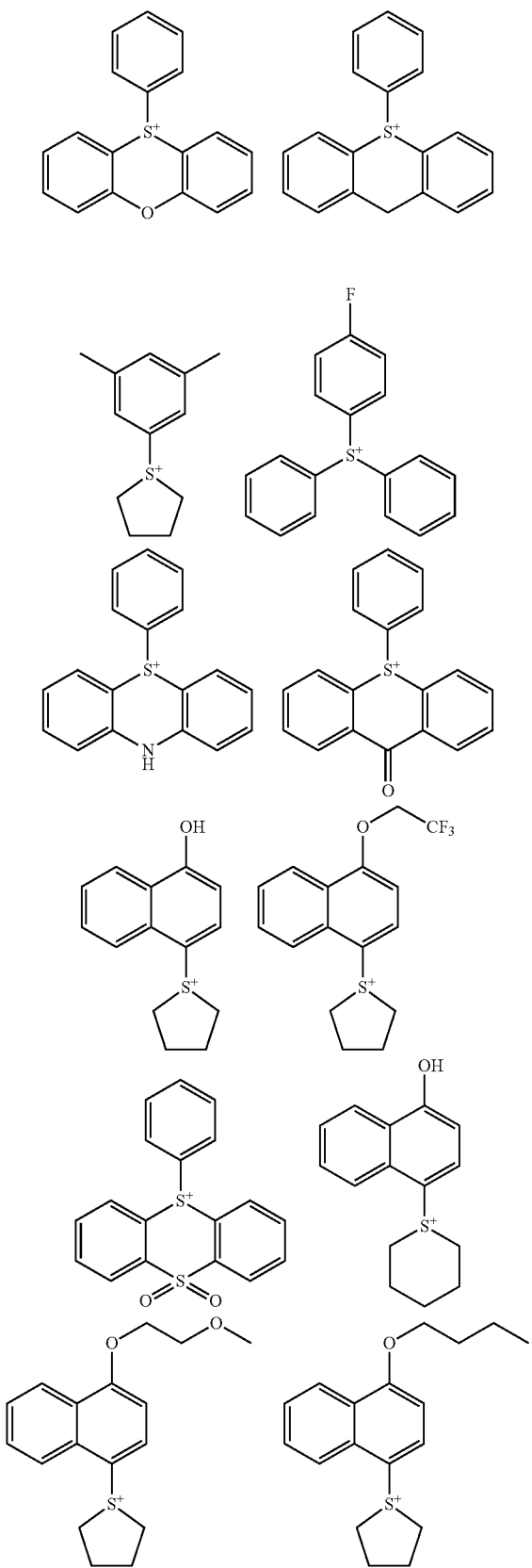

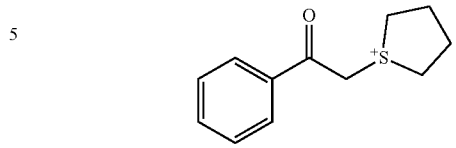

In an implementation, the iodonium cation represented by Formula 3 may include, e.g., cations of diphenyliodonium, bis(4-methylphenyl)iodonium, bis(4-ethylphenyl)iodonium, bis(4-(1,1-dimethylethyl)phenyl)iodonium, bis(4-(1,1-dimethylpropyl)phenyl)iodonium, bis(4-tert-butylphenyl)iodonium, bis(4-(1,1-dimethylpropyl)phenyl)iodonium, (4-(1,1-dimethylethoxy)phenyl)phenyliodonium, 4-methoxyphenylphenyliodonium, 4-tert-butoxyphenylphenyliodonium, 4-acryloyloxyphenylphenyliodonium, or 4-(meth)acryloyl oxyphenylphenyliodonium.

In an implementation, the ammonium cation represented by Formula 4 may include, e.g., tertiary ammonium cations, such as cations of trimethylammonium, triethylammonium, tributylammonium, and N,N-dimethylanilinium; or quaternary ammonium cations, such as cations of tetramethylammonium, tetraethylammonium, and tetrabutylammonium.

The photo-decomposable compound represented by Formula 1 may include a material (e.g., may be a compound) that generates an acid having an acid dissociation constant (pKa) of about 1 to about 10 upon exposure.

In Formula 1, an ester group (—O—C(=O)—) connected between a Ra group and a $Y^a$ group may affect electronic characteristics of the $R^a$ group. In an implementation, the ester group (—O—C(=O)—) connected between the $R^a$ group and the $Y^a$ group may act as an electron withdrawing group on the $R^a$ group. In an implementation, an ether group (—O—), which is part of the ester group (—O—C(=O)—) connected between the $R^a$ group and the $Y^a$ group, may be connected to the $R^a$ group, and a carbonyl group (—C(=O)—), which is part of the ester group, may be connected between the ether group (—O—) and the $Y^a$ group. Although the ether group (—O—) is an electron donating group, the carbonyl group —C(=O)—) connected between the ether group (—O—) and the $Y^a$ group may be a strong electron-withdrawing group. Thus, the ester group (—O—C(=O)—) connected between the $R^a$ group and the $Y^a$ group may act as an electron withdrawing group on the $R^a$ group. Accordingly, when the photo-decomposable compound represented by Formula 1 is decomposed upon exposure, the $R^a$ group may remain as unstable acid that lacks electrons.

As used herein, the term "electron donating group" may indicate that atoms in a covalent bond have a high tendency to give up electrons shared by other atoms, and the term "electron withdrawing group" may indicate that the atoms in the covalent bond have a high tendency to attract electrons shared by other atoms.

In an implementation, a photo-decomposable compound according to embodiments may be, e.g., represented by the following Formula 1a:

[Formula 1a]

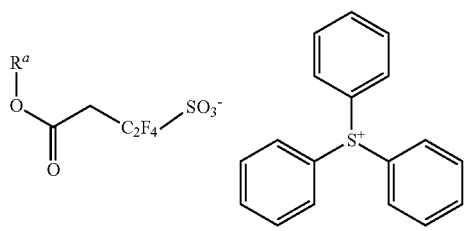

In Formula 1a, $R^a$ may be the same as defined in Formula 1. In an implementation, $R^a$ may be a monocyclic or condensed hydrocarbon group containing a nitrogen atom as a heteroatom.

In an implementation, the photo-decomposable compound according to embodiments may be, e.g., represented by one of the following Formulae 5 to 8.

[Formula 5]

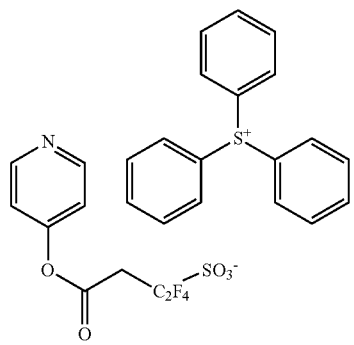

[Formula 6]

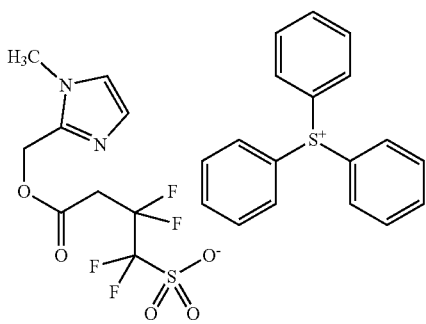

[Formula 7]

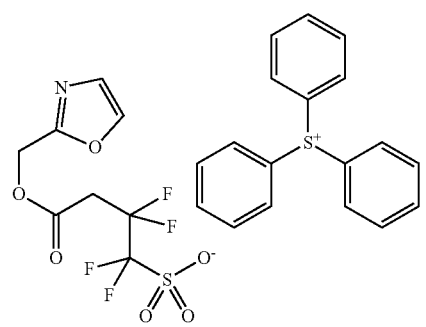

[Formula 8]

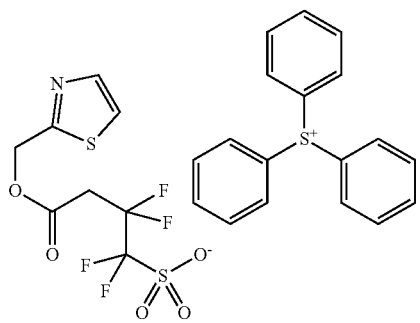

A photoresist composition according to embodiments may include, e.g., a chemically amplified polymer, a photoacid generator (PAG), a photo-decomposable compound, and a solvent. The photo-decomposable compound may generate acid upon exposure and act as a quenching base that neutralizes acid before exposure or in an unexposed state. The photo-decomposable compound may be represented by Formula 1, and a detailed description of the photo-decomposable compound may be the same as given above. In the photoresist composition according to the embodiments, the photo-decomposable compound may be contained at a content of about 0.1% to about 5.0% by weight, based on a total weight of the chemically amplified polymer.

In the photoresist composition according to the embodiments, the chemically amplified polymer may include a polymer including a repeating unit of which solubility in a developer may be changed by an action of an acid. The chemically amplified polymer may be a block copolymer or a random copolymer. In an implementation, the chemically amplified polymer may include positive-type photoresist. The positive-type photoresist may be, e.g., KrF excimer laser (248 nm) resist, ArF excimer laser (193 nm) resist, $F_2$ excimer laser (157 nm) resist, or EUV (13.5 nm) resist.

In an implementation, the chemically amplified polymer may include a repeating unit, which is decomposed by an action of an acid and increases solubility in an alkali developer. In an implementation, the chemically amplified polymer may include a repeating unit, which is decomposed by an action of an acid and generates phenolic acid or BrØnsted acid corresponding to the phenolic acid. In an implementation, the chemically amplified polymer may include a first repeating unit, which is derived from hydroxystyrene or derivatives thereof. The derivatives of hydroxystyrene may include hydroxystyrenes in which a hydrogen atom at an a position is substituted with a C1 to C5 alkyl group or a C1 to C5 halogenated alkyl group, and derivatives thereof. For example, the first repeating unit may be derived from 3-hydroxystyrene, 4-hydroxystyrene, 5-hydroxy-2-vinylnaphtalene, or 6-hydroxy-2-vinylnaphtalene.

In an implementation, the chemically amplified polymer may have a structure in which the first repeating unit derived from hydroxystyrene or the derivatives thereof is copolymerized with at least one second repeating unit having an acid-labile group. The at least one second repeating unit may include a (meth)acrylate-based polymer. In an implementation, the at least one second repeating unit may include polymethyl methacrylate (PMMA), poly(t-butylmethacrylate), poly(methacrylic acid), poly(norbornyl methacrylate), or a binary or ternary copolymer of repeating units of the (meth)acrylate-based polymers.

In an implementation, the chemically amplified polymer may include a blend of a first polymer having the first repeating unit and a second polymer having the at least one second repeating unit.

In an implementation, the acid-labile group, which may be included in the at least one second repeating unit, may include, e.g., tert-butoxycarbonyl (t-BOC), isonorbornyl, 2-methyl-2-adamantyl, 2-ethyl-2-adamantyl, 3-tetrahydrofuranyl, 3-oxocyclohexyl, γ-butyllactone-3-yl, mavaloniclactone, γ-butyrolactone-2-yl, 3-methyl-γ-butyrolactone-3-yl, 2-tetrahydropyranyl, 2-tetrahydrofuranyl, 2,3-propylenecarbonate-1-yl, 1-methoxyethyl, 1-ethoxyethyl, 1-(2-methoxyethoxy)ethyl, 1-(2-acetoxyethoxy)ethyl, t-buthoxycarbonylmethyl, methoxymethyl, ethoxymethyl, trimethoxysilyl, or triethoxysilyl.

In an implementation, the chemically amplified polymer may further include at least one of a third repeating unit having an acrylate derivative substituent including a hydroxy group (—OH) and a fourth repeating unit having a protecting group substituted with fluorine.

The chemically amplified polymer may have a weight-average molecular weight of about 1,000 to about 500,000. In the photoresist composition, the chemically amplified polymer may be contained at a content of about 1% to about 25% by weight, based on the total weight of the photoresist composition. Maintaining the content of the chemically amplified polymer at about 1% by weight or greater may help ensure that the photoresist composition may be smoothly coated. Maintaining the content of the chemically amplified polymer at about 25% by weight or less may help ensure that the viscosity of the photoresist composition is not excessively increased, facilitating uniform coating of the photoresist composition.

In the photoresist composition according to the embodiments, the PAG may include a material having a different chemical structural formula from the photo-decomposable compound. In an implementation, the PAG may generate acid when exposed to any one of a KrF excimer laser (248 nm), an ArF excimer laser (193 nm), an $F_2$ excimer laser (157 nm), and an EUV laser (13.5 nm). The PAG may include a material that generates a relatively strong acid having a pKa of, e.g., about −20 to about 1 upon exposure. The PAG may include, e.g., triarylsulfonium salts, diaryliodonium salts, sulfonates, or a mixture thereof. For example, the PAG may include triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, triphenylsulfonium perfluorobutanesulfonate, triphenylsulfonium perfluorooctanesulfonate (PFOS), diphenyliodonium PFOS, methoxydiphenyliodonium PFOS, di-t-butyldiphenyliodonium triflate, N-hydroxysuccinimide PFOS, norbornene-dicarboximide PFOS, or a mixture thereof.

In the photoresist composition according to the embodiments, the PAG may be contained at a content of about 0.1% to about 5.0% by weight, based on a total weight of the chemically amplified polymer.

In the photoresist composition according to the embodiments, the solvent may include an organic solvent. In an implementation, the solvent may include an, e.g., ether, alcohol, glycol ether, an aromatic hydrocarbon compound, ketone, or ester. In an implementation, the solvent may include, e.g., ethylene glycol monomethylether, ethylene glycol monoethylether, methyl cellosolve acetate, ethyl cellosolve acetate, diethylene glycol monomethylether, diethylene glycol monoethylether, propylene glycol, propylene glycol monomethylether, propylene glycol monomethyl etheracetate, propylene glycol monoethylether, propylene glycol monoethyletheracetate, propylene glycol propyletheracetate, propylene glycol monobutylether, propylene glycol monobutyl etheracetate, toluene, xylene, methylethyl ketone, cyclopentanone, cyclohexanone, 2-hydroxypropionate ethyl, 2-hydroxy-2-methylpropionate ethyl, ethyl ethoxyacetate, ethyl hydroxyacetate, 2-hydroxy-3-methylbutanoate methyl, 3-methoxypropionate methyl, 3-methoxypropionate ethyl, 3-ethoxypropionate ethyl, 3-ethoxypropionate methyl, methyl pyruvate, ethyl pyruvate, ethyl acetate, butyl acetate, ethyl lactoate, or butyl lactoate. The solvents may be used alone or in combination of at least two thereof. In an implementation, the amount of the solvent in the photoresist composition may be adjusted so that a solid content of the photoresist composition may range from about 3% to 20% by weight.

In an implementation, the photoresist composition according to the embodiments may further include an organic base including aliphatic amine, a surfactant, or a combination thereof. The organic base may include, e.g., primary amine, secondary amine, or tertiary amine. In an implementation, the organic base may include, e.g., triethanol amine, triethyl amine, tributyl amine, tripropyl amine, hexamethyl disilazan, or a combination thereof. In the photoresist composition according to the embodiments, the organic base may be contained at a content of about 0.01% to about 5.0% by weight, based on the total weight of the chemically amplified polymer. In an implementation, the surfactant may include, e.g., fluoroalkyl benzenesulfonate, fluoroalkyl carboxylate, fluoroalkyl polyoxyethyleneether, fluoroalkyl ammonium iodide, fluoroalkyl betaine, fluoroalkyl sulfonate, diglycerin tetrakis(fluoroalkyl polyoxyethyleneether), fluoroalkyl trimethylammonium salt, fluoroalkyl aminosulfonate, polyoxyethylene nonylphenylether, polyoxyethylene octylphenylether, polyoxyethylene alkylether, polyoxyethylene laurylether, polyoxyethylene oleylether, polyoxyethylene tridecylether, polyoxyethylene cetylether, polyoxyethylene stearylether, polyoxyethylene laurate, polyoxyethylene oleate, polyoxyethylene stearate, polyoxyethylene laurylamine, sorbitan laurate, sorbitan palmitate, sorbitan stearate, sorbitan oleate, sorbitan fatty acid ester, polyoxyethylene sorbitan laurate, polyoxyethylene sorbitan palmitate, polyoxyethylene sorbitan stearate, polyoxyethylene sorbitan oleate, polyoxyethylene naphthylether, alkylbenzene sulfonate, or alkyldiphenylether disulfonate. The surfactant may be contained at a content of about 0.001% to about 0.1% by weight, based on the total weight of the chemically amplified polymer.

In the photoresist composition according to the embodiments, an acid may be generated from each of the PAG and the photo-decomposable compound upon exposure. In an implementation, the PAG may include a material that generates a first acid having a first pKa upon exposure, and the photo-decomposable compound may generate a second acid having a second pKa upon exposure. In an implementation, the second pKa may be higher than the first pKa. In an implementation, a pKa of the first acid generated from the PAG may be, e.g., about −20 to about 1, and a pKa of the second acid generated from the photo-decomposable compound may be, e.g., about 1 to about 10.

In an implementation, the PAG may be, e.g., a compound of one of the following Formulae 9 to 18.

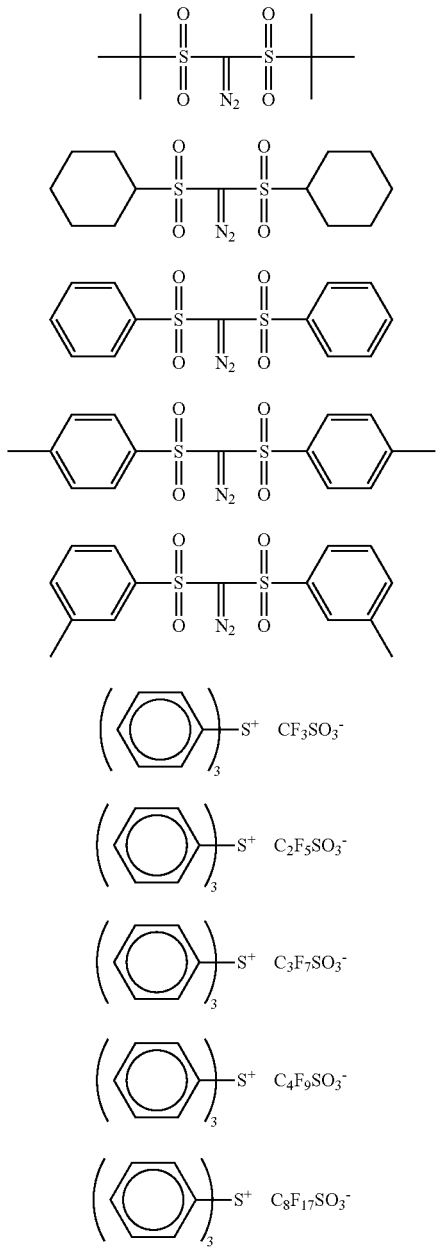

[Formula 9]
[Formula 10]
[Formula 11]
[Formula 12]
[Formula 13]
[Formula 14]
[Formula 15]
[Formula 16]
[Formula 17]
[Formula 18]

From among the PAGs of Formulae 9 to 18, the PAGs of Formulae 9 to 13 may generate acids having a pKa of about −3 in response to light. The PAGs of Formulae 14 to 18 may generate acids having a pKa of about −10 in response to light.

In an implementation, when a compound including pyridine, which is shown in Formula 5, is used as the photo-decomposable compound, the photo-decomposable compound may generate a pyridinium cation in response to light. The pyridinium cation may have a pKa of about 3.4. The pyridinium cation may be a strong acid, which is stronger than acetic acid (having a pKa of about 12.3). Accordingly, the pyridinium cation may act on an acid-labile protecting group of the chemically amplified polymer and may deprotect the chemically amplified polymer.

As described above, in the photoresist composition according to the embodiments, relatively strong acids may be respectively generated from the PAG and the photo-decomposable compound upon exposure and may act on a protecting group of the chemically amplified polymer to deprotect the chemically amplified polymer. Thus, the deprotected polymer may be changed into an alkali soluble group.

A vast amount of research has been conducted into an EUV lithography technique incorporating an exposure process using EUV light having a wavelength of about 13.5 nm as an advanced technique for superseding a lithography process using a KrF excimer laser (248 nm) and an ArF excimer laser (193 nm). An EUV lithography process may be based on a different action mechanism from the lithography process using the KrF excimer laser and the ArF excimer laser. The entire EUV lithography process may be performed in vacuum. In an EUV lithography system, power required for a light source to irradiate laser light may be insufficient. There may be a specific limit to sufficiently increasing a dose to generate a required amount of acid from a PAG, from among components of a photoresist composition, during an exposure process. When an EUV lithography process is performed using some photoresist compositions including only a PAG, acid generation efficiency and an exposure speed may be reduced due to a relatively low dose provided by a light source of the EUV lithography system. Accordingly, it may be difficult to obtain a desired exposure sensitivity.

The photoresist composition according to the embodiments may include not only the PAG but also the photo-decomposable compound, and the photo-decomposable compound may generate acid upon exposure and also act as a quenching base that neutralizes acid. Accordingly, when a photoresist film formed using the photoresist composition is exposed, an acid may be generated from each of the PAG and the photo-decomposable compound in an exposed area of the photoresist film. Also, the photo-decomposable compound may act as a quenching base to neutralize acid in a non-exposed area of the photoresist film. Thus, a difference in acidity between the exposed area and the non-exposed area of the photoresist film may be increased. Accordingly, a difference in solubility in the developer between the exposed area and the non-exposed area of the photoresist film may be increased. As a result, a high pattern fidelity may be achieved by reducing a line edge roughness (LER) and a line width roughness (LWR) in a photoresist pattern obtained by developing the exposed photoresist film.

Hereinafter, a method of manufacturing an integrated circuit (IC) device according to an example embodiment will be described.

FIG. 1 is a flowchart of a method of manufacturing an IC device, according to embodiments. FIGS. 2A to 2F are cross-sectional views of stages in a method of manufacturing an IC device, according to embodiments.

Figure 2A:
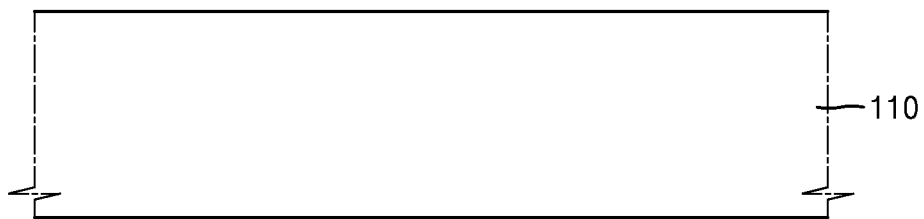
FIGS. 2A to 2F are cross-sectional views of stages in a method of manufacturing an IC device, according to embodiments.

Referring to FIGS. 1 and 2A, in process P10A of FIG. 1, a feature layer 110 may be prepared.

In an implementation, the feature layer 110 may include a semiconductor substrate. In an implementation, the feature layer 110 may include a semiconductor, such as silicon (Si) or germanium (Ge), or a compound semiconductor, such as silicon germanium (SiGe), silicon carbide (SiC), gallium arsenide (GaAs), indium arsenide (InAs), or indium phosphide (InP). In an implementation, the feature layer 110 may include a conductive film, a dielectric film, an insulating film, or a combination thereof, which is formed on the semiconductor substrate. In an implementation, the feature layer 110 may include a metal, an alloy, a metal carbide, a metal nitride, a metal oxynitride, a metal oxycarbide, a semiconductor, polysilicon, oxide, nitride, oxynitride, or a combination thereof.

Figure 2B:
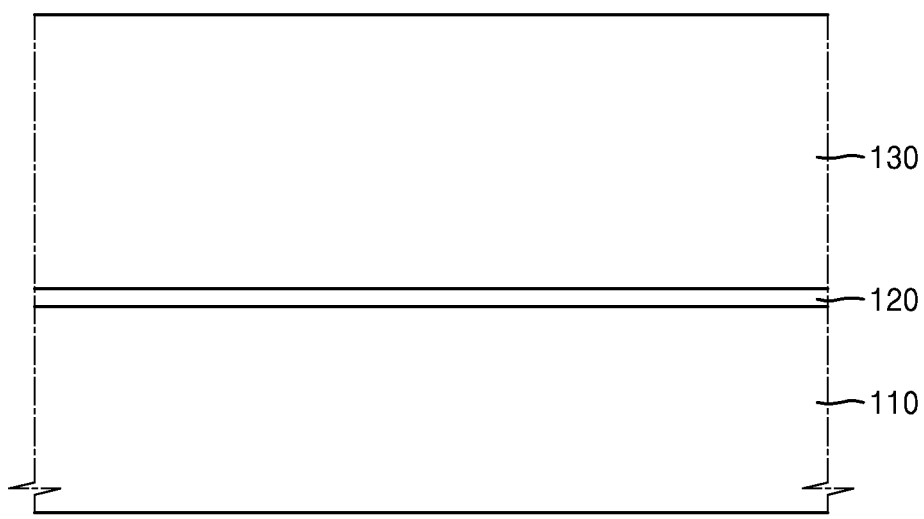

Referring to FIGS. 1 and 2B, in process P10B, a photoresist film 130 may be formed on a feature layer 110.

In an implementation, before the photoresist film 130 is formed on the feature layer 110, a developable bottom anti-reflective coating (DBARC) film 120 may be formed on the feature layer 110, and the photoresist film 130 may be formed on the DBARC film 120. The DBARC film 120 may help control scattering reflection of light from a light source used during an exposure process for manufacturing an IC device or absorb reflected light from the feature layer 110 located thereunder. In an implementation, the DBARC film 120 may include an organic anti-reflective coating (ARC) material for a KrF excimer laser, an ArF excimer laser, or any other light source. In an implementation, the DBARC film 120 may include an organic component having a light-absorbing structure. The light-absorbing structure may include, e.g., at least one benzene ring or a hydrocarbon compound in which benzene rings are fused. In an implementation, the DBARC film 120 may be formed to a thickness of, e.g., about 20 nm to about 100 nm.

To form the photoresist film 130, the DBARC film 120 may be coated with a photoresist composition according to an embodiment, and an annealing process may be performed. The coating process may be performed using, e.g., a spin coating process, a spray coating process, and a dip coating process. The process of annealing the photoresist composition may be performed, e.g., at a temperature of about 80° C. to about 150° C. for about 10 seconds to about 100 seconds. A thickness of the photoresist film 130 may be several times to several hundred times a thickness of the DBARC film 120. In an implementation, the photoresist film 130 may be formed to a thickness of, e.g., about 100 nm to about 6 m.

Figure 2C:
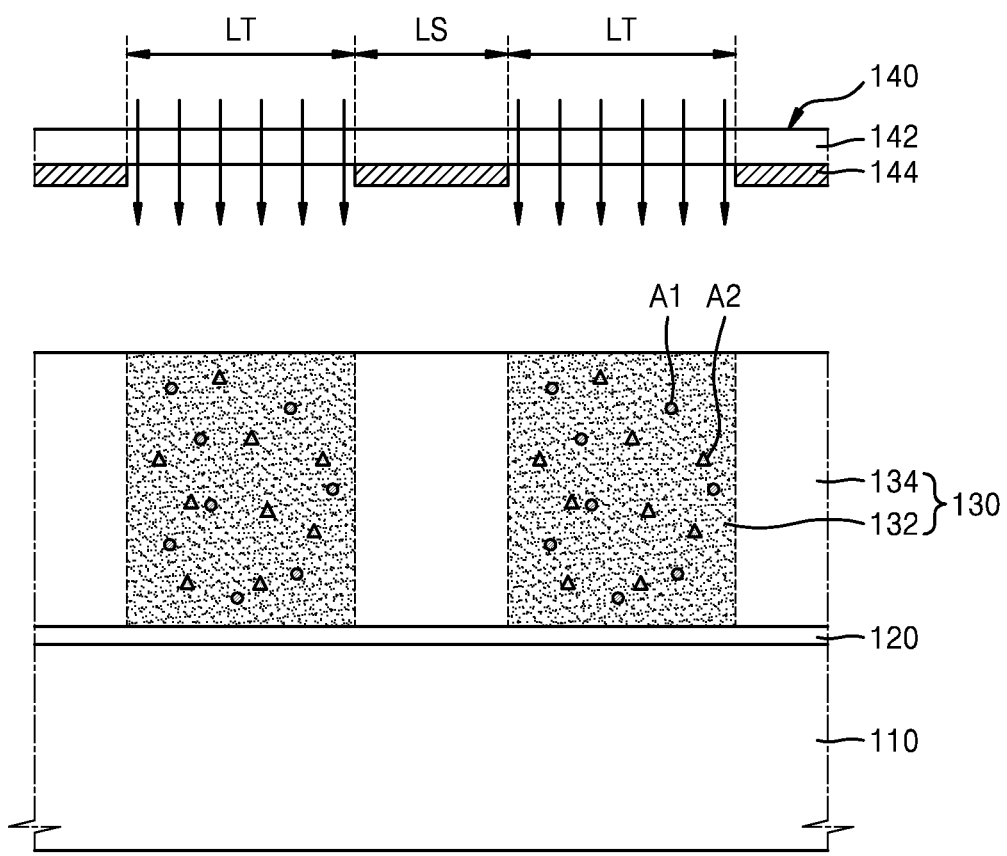

Referring to FIGS. 1 and 2C, in process P10C, a first area 132, which is a portion of the photoresist film 130, may be exposed to generate a plurality of first acids A1 and a plurality of second acids A2 in the first area 132 of the photoresist film 130. The plurality of first acids A1 may be derived from the PAG, and the plurality of second acids A2 may be derived from the photo-decomposable compound.

To expose the first area 132 of the photoresist film 130, a photomask 140 having a plurality of light-shielding areas LS and a plurality of light-transmitting areas LT may be aligned at a predetermined position on the photoresist film 130, and the first area 132 of the photoresist film 130 may be exposed through the plurality of light-transmitting areas LT of the photomask 140. The first area 132 of the photoresist film 130 may be exposed using a KrF excimer laser (248 nm), an ArF excimer laser (193 nm), a $F_2$ excimer laser (157 nm), or an EUV laser (13.5 nm).

The photomask 140 may include a transparent substrate 142 and a plurality of light-shielding patterns 144 in the plurality of light-shielding areas LS on the transparent substrate 142. The transparent substrate 142 may include quartz. The plurality of light-shielding patterns 144 may include chromium (Cr). The plurality of light-transmitting areas LT may be defined by the plurality of light-shielding patterns 144.

The plurality of second acids A2 generated from the photo-decomposable compound may be weaker than the plurality of first acids A1 generated from the PAG. In an implementation, the PAG may generate the first acid A1 having a first pKa upon exposure, and the photo-decomposable compound may generate the second acid A2 having a second pKa upon exposure. The second pKa may be higher than the first pKa. In an implementation, the first pKa of the first acid A1 generated by the PAG may be, e.g., about −20 to about 1, and the second pKa of the second acid A2 generated by the photo-decomposable compound may be, e.g., about 1 to about 10.

In an implementation, an annealing process may be performed to diffuse the plurality of first acids A1 and the plurality of second acids A2 in the first area 132 of the photoresist film 130. In an implementation, the resultant structure, which is obtained directly after the first area 132 of the photoresist film 130 is exposed in process P10C of FIG. 1, may be annealed at a temperature of about 50° C. to about 150° C. Thus, at least some of the plurality of first acids A1 and the plurality of second acids A2 may be diffused in the first area 132 of the photoresist film 130 so that the plurality of first acids A1 and the plurality of second acids A2 may be relatively uniformly distributed in the first area 132 of the photoresist film 130. The annealing process may be performed for about 10 seconds to about 100 seconds. In an implementation, the annealing process may be performed at a temperature of about 100° C. for about 60 seconds.

In an implementation, an additional annealing process may not be performed to diffuse the plurality of first acids A1 and the plurality of second acids A2 in the first area 132 of the photoresist film 130. In this case, in process P10C of FIG. 1, during the exposing of the first area 132 of the photoresist film 130, the plurality of first acids A1 and the plurality of second acids A2 may be diffused in the first area 132 of the photoresist film 130 without an additional annealing process.

As a result of the diffusion of the plurality of first acids A1 and the plurality of second acids A2 in the first area 132 of the photoresist film 130, an acid-labile group in a chemically amplified polymer included in the photoresist film 130 may be deprotected in the first area 132 of the photoresist film 130, and thus, the first area 132 of the photoresist film 130 may be changed to a state in which the first area 132 may be easily dissolved in an alkali developer.

In the first area 132 that is an exposed area, the photo-decomposable compound included in the photoresist film 130 may be decomposed due to exposure and may not act as a quenching base that neutralizes the plurality of first acids A1 generated from the PAG. In contrast, because light is not transmitted to the PAG and the photo-decomposable compound, which are included in the photoresist film 130, in a second area 134 that is a non-exposed area of the photoresist film 130, acid may not be generated from the PAG and the photo-decomposable compound. Thus, a reaction of deprotection of the acid-labile group from the chemically amplified polymer may not occur in the second area 134 of the photoresist film 130. Also, the photo-decomposable compound included in the second area 134, which is the non-exposed area of the photoresist film 130, may not be decomposed but remain as a base. Accordingly, in the second area 134 that is the non-exposed area, the photo-decomposable compound included in the photoresist film 130 may act as a quenching base to neutralize any acids that have been undesirably diffused from the first area 132 into or are otherwise present in the second area 134.

As described above, the plurality of first acids A1, which are generated from the PAG, and the plurality of second acids A2, which are generated from the photo-decomposable compound, may be present in the first area 132 (e.g., the exposed area). The photo-decomposable compound serving as the quenching base for neutralizing acid may be present in an undecomposed state in the second area 134 (e.g., the non-exposed area). Thus, a difference in acidity between the exposed first area 132 and the non-exposed second area 134, may be increased. Accordingly, a difference in solubility in a developer between the exposed area and the non-exposed area of the photoresist film 130 may be increased. As a result, a pattern having a low LER or a low LWR may be obtained in a final pattern, which is to be formed in a subsequent process.

Figure 2D:
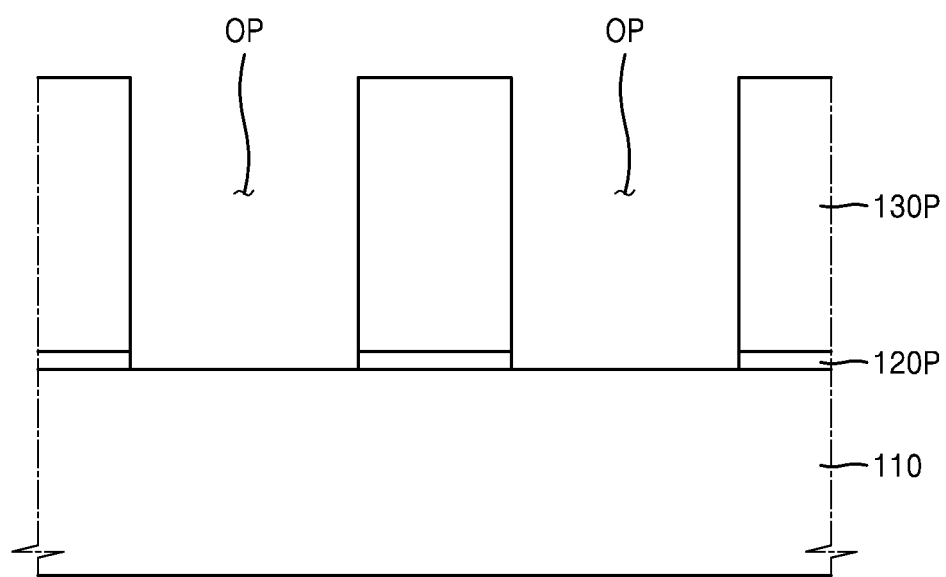

Referring to FIGS. 1 and 2D, in process P10D, the photoresist film 130 may be developed using an alkali developer to remove the first area 132 from the photoresist film 130. As a result, a photoresist pattern 130P including the second area 134, which is the non-exposed area, may be formed.

The photoresist pattern 130P may include a plurality of openings OP. A portion of the DBARC film 120, which is exposed through the plurality of openings OP, may be removed to form a DBARC pattern 120P.

The alkali developer may include 2.38% by weight of a tetramethylammonium hydroxide (TMAH) solution. The chemically amplified polymer may be deprotected by the plurality of first acids A1 and the plurality of second acids A2 in the first area 132 of the photoresist film 130, the first area 132 may be cleanly removed during the developing of the photoresist film 130 by using the alkali developer. Accordingly, after the photoresist film 130 is developed, residue defects, such as a footing phenomenon, may not occur, and the photoresist pattern 130P may obtain a vertical sidewall profile. As described above, by improving a profile of the photoresist pattern 130P, when the feature layer 110 is processed using the photoresist pattern 130P, a critical dimension (CD) of an intended processing region may be precisely controlled in the feature layer 110.

Figure 2E:
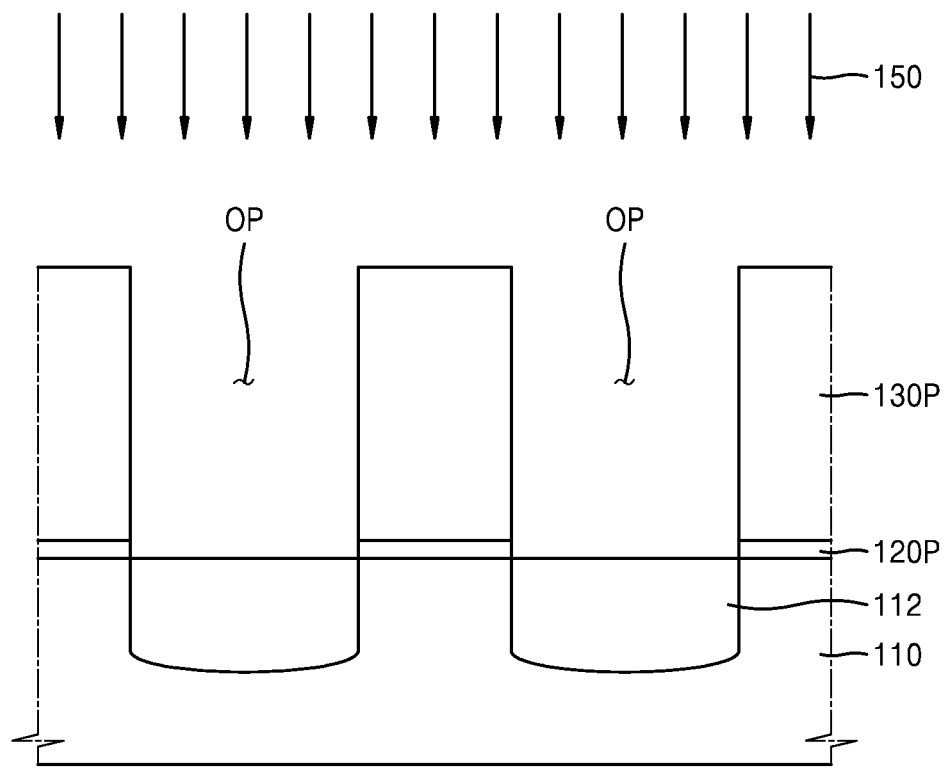

Referring to FIGS. 1 and 2E, in process P10E, the feature layer 110 may be processed using the photoresist pattern 130P.

In an implementation, various processes including a process of implanting impurity ions into the feature layer 110 through the plurality of openings OP of the photoresist pattern 130P, a process of etching the feature layer 110 through the plurality of openings OP, a process of forming an additional film on the feature layer 110 through the plurality of openings OP, and a process of modifying a portion of the feature layer 110 through the plurality of openings OP may be performed.

FIG. 2E illustrates an ion implantation process as an example of processing the feature layer 110 exposed through the plurality of openings OP. As shown in FIG. 2E, impurity ions 150 may be implanted into the feature layer 110 through the plurality of openings OP, thereby forming a plurality of wells 112 in the feature layer 110. Each of the plurality of wells 112 may include an impurity region into which the impurity ions 150 are implanted. The impurity ions 150 may be an n-type dopant or a p-type dopant.

Figure 2F:
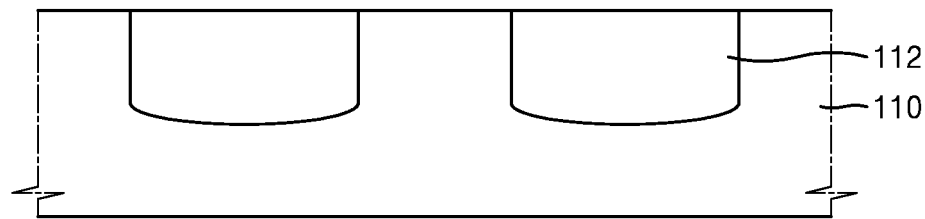

Referring to FIG. 2F, the photoresist pattern 130P and the DBARC pattern 120P, which remain on the feature layer 110, may be removed from the resultant structure of FIG. 2E. The photoresist pattern 130P and the DBARC pattern 120P may be removed using an ashing process and a strip process.

In the method of manufacturing the photoresist film 130 including the photo-decomposable compound according to the embodiments described with reference to FIGS. 1 and 2A to 2F, a difference in acidity between the exposed area and the non-exposed area of the photoresist film 130 including the photo-decomposable compound according to the embodiments may be increased to increase solubility in the developer between the exposed area and the non-exposed area. Thus, an LER and an LWR may be reduced in the photoresist pattern 130P obtained from the photoresist film 130 to provide a high pattern fidelity. Accordingly, when a subsequent process is performed on the feature layer 110 using the photoresist pattern 130P, a dimensional precision may be improved by precisely controlling critical dimensions of processing regions or patterns to be formed in the feature layer 110.

The following Examples are provided in order to highlight characteristics of one or more embodiments, but it will be understood that the Examples are not to be construed as limiting the scope of the embodiments. Further, it will be understood that the embodiments are not limited to the particular details described in the Examples.

Synthesis Example 1

Synthesis of Photo-Decomposable Compound of Formula 5

The compound (triphenylsulfonium 1,1,2,2-tetrafluoro-4-oxo-4-[(pyridin-4-yl)oxy]butane-1-sulfonate) of Formula 5 was synthesized according to Chemical equations 1a, 1b, and 1c. To this end, 4-bromo-3,3,4,4-tetrafluorobutanoic acid was initially synthesized according to Chemical equation 1a.

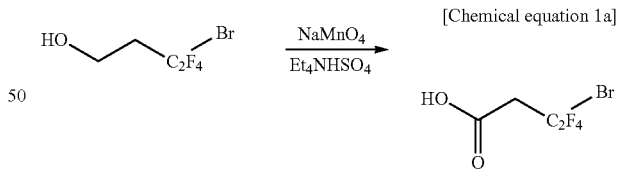

[Chemical equation 1a]

The synthesis process shown in Chemical equation 1a will now be described. A solution obtained by dissolving 30 g (113 mmol) of 4-bromo-3,3,4,4-tetrafluorobutanol and 34 mg (0.1 mmol) of tetraethyllammonium hydrogensulfate in 150 ml of distilled water was put in a 3-neck flask equipped with a cooling pipe and a thermometer. 29.8 g (187 mmol) of sodium permanganate hydrate and 100 ml of a distilled aqueous solution were slowly added to the solution to cause a reaction at a temperature of 65° C. for 5 hours. The reacted solution was cooled to ambient temperature, a precipitate was filtered from the reacted solution, and the resultant filtrate was washed twice with diethyl ether. An aqueous solution layer was acidified to a pH value of 1 using dilute sulfuric acid. The obtained aqueous solution was transferred to a separatory funnel, extracted three times with 100 ml of diethyl ether to combine organic layers. Thereafter, the combined organic layer was dried with dehydrated magnesium sulfate and filtered. The resultant product was desolventized using a rotary evaporator to obtain 25.7 g of 4-bromo-3,3,4,4-tetrafluorobutanoic acid (yield 81%).

$^1$H NMR (300 MHz, DMSO-d$^6$) δ: 12.01 (s, 1H), 2.53 (t, 2H)

A synthesis process shown in Chemical equation 1b was performed using 4-bromo-3,3,4,4-tetrafluorobutanoic acid obtained in Chemical equation 1a:

[Chemical equation 1b]

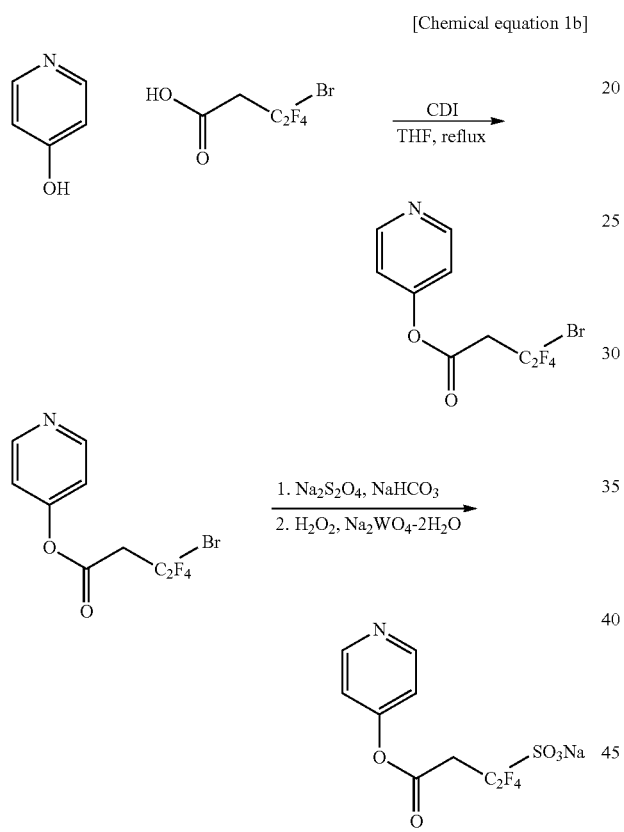

The synthesis process shown in Chemical equation 1b will now be described in further detail. 10 g (42 mmol) of 4-bromo-3,3,4,4-tetrafluorobutanoic acid obtained in Chemical equation 1a was put in a 250-mL flask, and the 250-mL flask was filled with 100 mL of a dehydrated tetrahydrofuran (THF) solvent under an $N_2$ atmosphere. A solution in which 7.5 g (46 mmol) of 1',1'-carbodiimidazole (CDI) was dissolved in 20 mL of dehydrated THE was slowly added dropwise to the obtained solution at ambient temperature. The resultant product was stirred for 3 hours, and 4 g (42 mmol) of 4-hydroxypyridine was slowly added dropwise while heating and refluxing the same. The resultant product was refluxed for 12 hours and cooled to ambient temperature, and layer separation was caused in a separatory funnel by putting ethyl acetate and water therein. An organic layer (i.e., an ethyl acetate layer) at an upper position was washed with distilled water three times, dried with dehydrated magnesium sulfate, and filtered. The resultant product was desolventized using a rotary evaporator. The obtained organic material was dissolved in 100 mL of acetonitrile and 100 mL of distilled water in a 500-mL flask. 17.7 g (102 mmol) of sodium hydrosulfite and 12.9 g (153 mmol) of sodium bicarbonate were put in the 500-mL flask and stirred while heating the same at a temperature of 60° C. for 20 hours. Thereafter, the resultant product was cooled to room temperature, and an organic layer was separated and transferred to a 500-mL flask. Afterwards, 100 mL of distilled water, 8.7 g (76 mmol) of 30% hydrogen peroxide, and 40 mg (0.12 mmol) of sodium tungstate dihydrate were put in the 500-mL flask and stirred at ambient temperature for 6 hours. After a reaction was completed, 17.4 g (100 mmol) of sodium hydrosulfite was slowly added to the reacted solution to cause a reaction. Thereafter, the remaining hydrogen peroxide was reduced and removed, and a sodium chloride aqueous solution was put in the 500-mL flask to cause layer separation of an organic layer from an aqueous layer. 300 mL of diethyl ether was added to the resultant product and stirred to separate an organic layer, which was at an upper position, from the resultant product. The separated organic layer was dried with dehydrated magnesium sulfate and filtered, and the resultant product was then desolventized using a rotary evaporator, and a synthesis process shown in Chemical equation 1c was performed without an additional purification process.

[Chemical equation 1c]

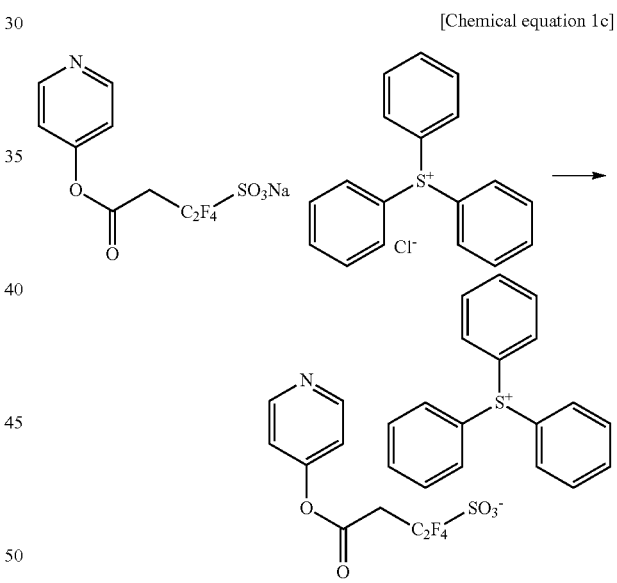

The synthesis process shown in Chemical equation 1c will now be described in detail. 10.9 g (32 mmol) of the compound (sodium 1,1,2,2-tetrafluoro-4-oxo-4-[(pyridin-4-yl)oxy]butane-1-sulfonate) obtained in Chemical equation 1b, 50 mL of dichloromethane, and 50 mL of distilled water were put in a 250-mL flask, 21.4 g (32.2 mmol) of triphenylsulfonium chloride (45% in water) was added to the 250-mL flask and stirred for 20 hours at ambient temperature. An organic layer (i.e., a dichloromethane layer) at a lower position was separated and cleaned with 100 mL of distilled water three times. Thereafter, the obtained organic layer was dried with dehydrated magnesium sulfate and filtered. The resultant product was desolventized using a rotary evaporator to be concentrated, and then dissolved again in 20 mL of dichloromethane. 40 mL of diethyl ether was put and cooled to obtain 16.5 g of the compound of Formula 5 (yield 89%).

$^1$H NMR (300 MHz, DMSO-d$^6$) δ: 8.42 (d, 2H), 7.40-7.15 (m, 17H), 2.56 (t, 2H)

Synthesis Example 2

Synthesis of Photo-Decomposable Compound of Formula 6

The compound (triphenylsulfonium 1,1,2,2-tetrafluoro-4-[(1-methyl-1H-imidazol-2-yl)methoxy]-4-oxobutane-1-sulfonate) of Formula 6 was synthesized according to Chemical equation 2.

[Chemical equation 2]

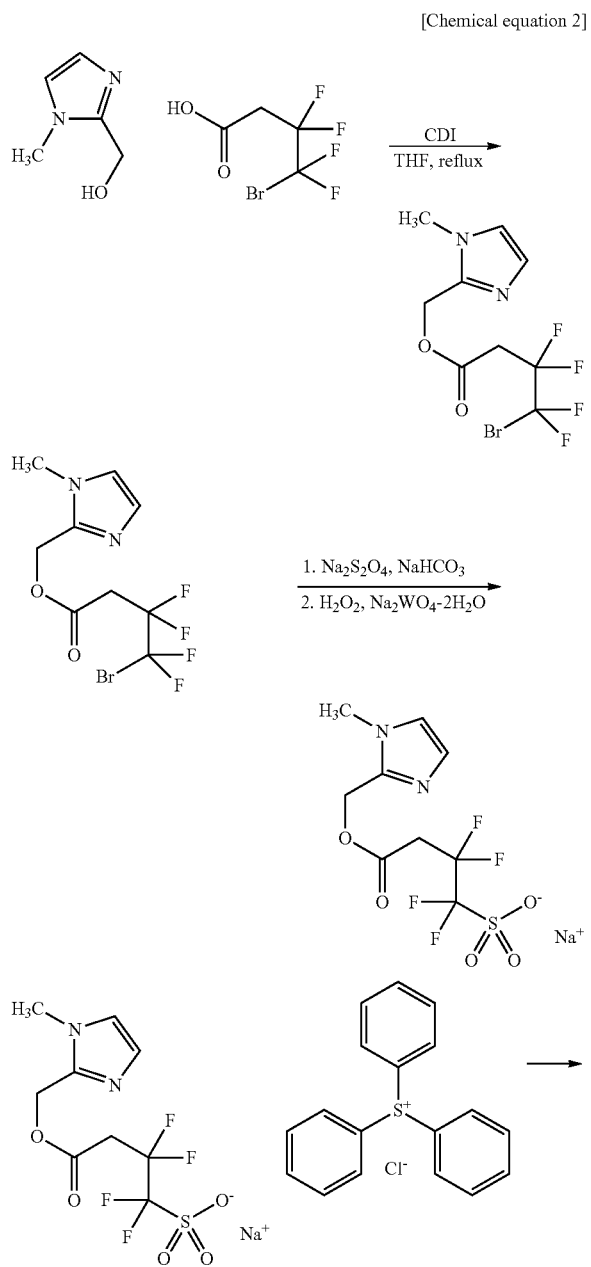
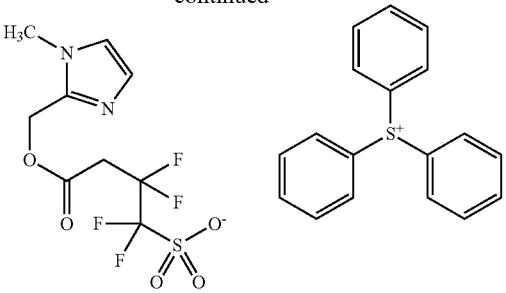

A synthesis process shown in Chemical equation 2 will now be described in detail. 10 g (42 mmol) of 4-bromo-3,3,4,4-tetrafluorobutanoic acid was put in a 250-mL flask, and the 250-mL flask was filled with 100 mL of a dehydrated THF solvent under an N$_2$ atmosphere. A solution in which 7.5 g (46 mmol) of CDI was dissolved in 20 mL of dehydrated THF was slowly added dropwise to the obtained solution at ambient temperature. The resultant product was stirred for three hours, and 4.69 g (42 mmol) of (1-methyl-1H-imidazol-2-yl)methanol was then slowly added dropwise while heating and refluxing the same. Thereafter, the resultant product was refluxed for 12 hours and cooled to ambient temperature, and layer separation was caused in a separatory funnel by putting ethyl acetate and water therein. An organic layer (i.e., an ethyl acetate layer) at an upper position was washed with distilled water three times, dried with dehydrated magnesium sulfate, and filtered. The resultant product was desolventized using a rotary evaporator. The obtained organic material was dissolved in 100 mL of acetonitrile and 100 mL of distilled water in a 500-mL flask. 17.7 g (102 mmol) of sodium hydrosulfite and 12.9 g (153 mmol) of sodium bicarbonate were put in the 500-mL flask and stirred while heating the same at a temperature of 60° C. for 20 hours. The resultant product was cooled to ambient temperature, and an organic layer was separated and transferred to a 500-mL flask. Afterwards, 100 mL of distilled water, 8.7 g (76 mmol) of 30% hydrogen peroxide, and 40 mg (0.12 mmol) of sodium tungstate dihydrate were put in the 500-mL flask and stirred at ambient temperature for 6 hours. After a reaction was completed, 17.4 g (100 mmol) of sodium hydrosulfite was slowly added to the reacted solution. After the reaction, the remaining hydrogen peroxide was removed by reduction, and a sodium chloride aqueous solution was put in the 500-mL flask to cause layer separation of an organic layer from an aqueous layer. 300 mL of diethyl ether was added to the resultant product and stirred to separate an organic layer, which was at an upper position, from the resultant product. The separated organic layer was dried with dehydrated magnesium sulfate and filtered, and the resultant product was then desolventized using a rotary evaporator to obtain an intermediate product sodium (1,1,2,2-tetrafluoro-4-[(1-methyl-1H-imidazol-2-yl)methoxy]-4-oxobutane-1-sulfonate). Afterwards, the following process was performed without an additional purification process.

11.4 g (32 mmol) of the intermediate product (sodium 1,1,2,2-tetrafluoro-4-[(1-methyl-1H-imidazol-2-yl)methoxy]-4-oxobutane-1-sulfonate), 50 mL of dichloromethane, and 50 mL of distilled water were put in a 250-mL flask, 21.4 g (32.2 mmol) of triphenylsulfonium chloride (45% in water) was added and stirred at ambient temperature for 20 hours. An organic layer (i.e., a dichloromethane layer) at a lower position was separated and washed with 100 mL of distilled water three times, dried with dehydrated magnesium sulfate, and filtered. The resultant product was desolventized using a rotary evaporator to be concentrated, and then dissolved again in 20 mL of dichloromethane. 40 mL of diethyl ether was put and cooled to obtain 17.8 g of the compound of Formula 6 (yield 93%).

$^1$H NMR (300 MHz, DMSO-d$^6$) δ: 7.35-6.71 (m, 17H), 5.27 (s, 2H), 3.72 (s, 3H), 2.53 (t, 2H)

Synthesis Example 3

Synthesis of Photo-Decomposable Compound of Formula 7

A compound (triphenylsulfonium 1,1,2,2-tetrafluoro-4-[(1,3-oxazol-2-yl)methoxy]-4-oxobutane-1-sulfonate) of Formula 7 was synthesized according to Chemical equation 3:

[Chemical equation 3]

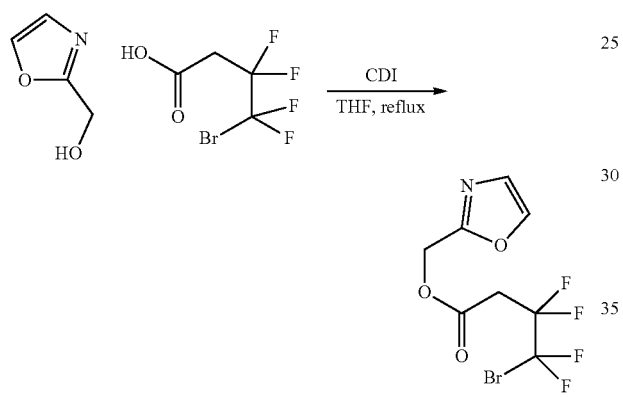

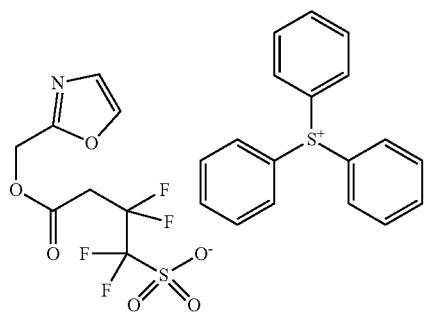

A synthesis process shown in Chemical equation 3 will now be described. The same process as in Synthesis example 2 was performed except that 4.16 g (42 mmol) of (1,3-oxazol-2-yl)methanol was used instead of 4.69 g (42 mmol) of (1-methyl-1H-imidazol-2-yl)methanol to obtain 16.2 g of the compound of Formula 7 (yield 87%).

$^1$H NMR (300 MHz, DMSO-d$^6$) δ: 7.60-7.15 (m, 17H), 5.30 (s, 2H), 2.57 (t, 2H)

Synthesis Example 4

Synthesis of Photo-Decomposable Compound of Formula 8

A compound (triphenylsulfonium 1,1,2,2-tetrafluoro-4-[(1,3-oxazol-2-yl)methoxy]-4-oxobutane-1-sulfonate) of Formula 8 was synthesized according to Chemical equation 4:

[Chemical equation 4]

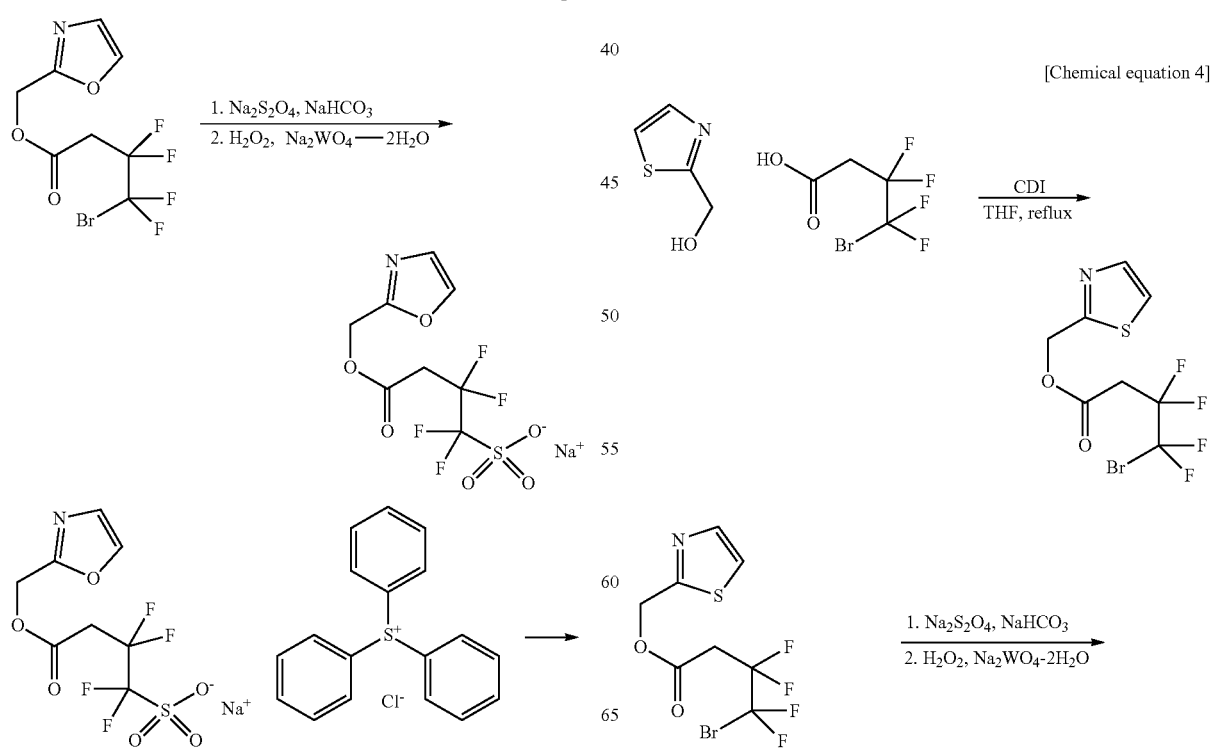

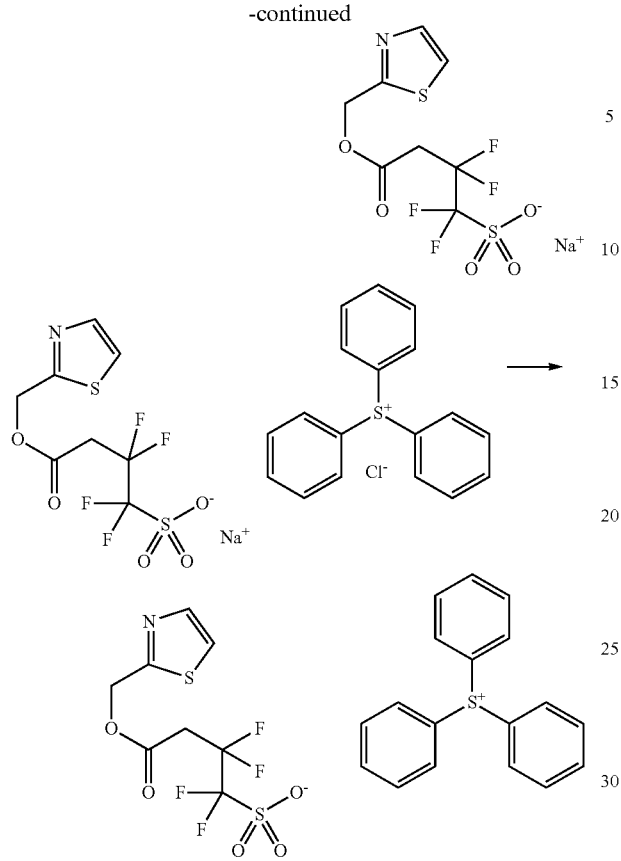

A synthesis process shown in Chemical equation 4 will now be described. The same process as in Synthesis example 2 was performed except that 4.84 g (42 mmol) of (1,3-thiazol-2-yl)methanol was used instead of 4.69 g (42 mmol) of (1-methyl-1H-imidazol-2-yl)methanol to obtain 17.3 g of the compound of Formula 8 (yield 90%).

$^1$H NMR (300 MHz, DMSO-d$^6$) δ: 7.71-7.33 (m, 17H), 5.34 (s, 2H), 2.55 (t, 2H)

By way of summation and review, a photolithography process including a positive tone development (PTD) process may use a technique for increasing a difference in acidity between an exposed area and a non-exposed area of a photoresist film while generating a relatively large amount of acid in the exposed area of the photoresist film with the same amount of light.

One or more embodiments may provide a photo-decomposable compound capable of neutralizing acid.

One or more embodiments may provide a photo-decomposable compound, which generates acid upon exposure and acts as a quenching base that neutralizes acid before exposure or in an unexposed region or state.

One or more embodiments may provide a photoresist composition, which may increase a difference in acidity between an exposed area and a non-exposed area of a photoresist film while generating a relatively large amount of acid in the exposed area of the photoresist film with the same amount of light during a photolithography process, and ensure a dimensional precision of a pattern to be formed.

One or more embodiments may provide a method of manufacturing an integrated circuit (IC) device, which may improve a dimensional precision of a pattern during a photolithography process and increase productivity.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A photo-decomposable compound represented by Formula 1:

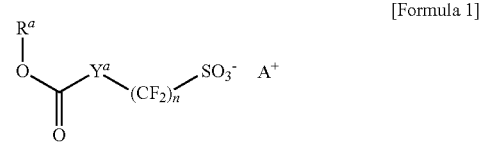

[Formula 1]

wherein, in Formula 1,
Y$^a$ is a C1 to C20 divalent linear or cyclic hydrocarbon group,
n is an integer of 1 to 5,
A$^+$ is a counter ion,
R$^a$ is one of the following groups:

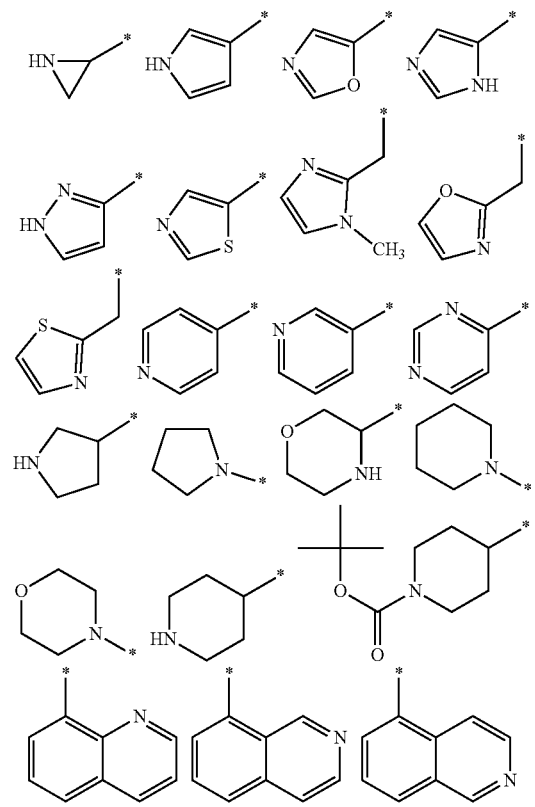

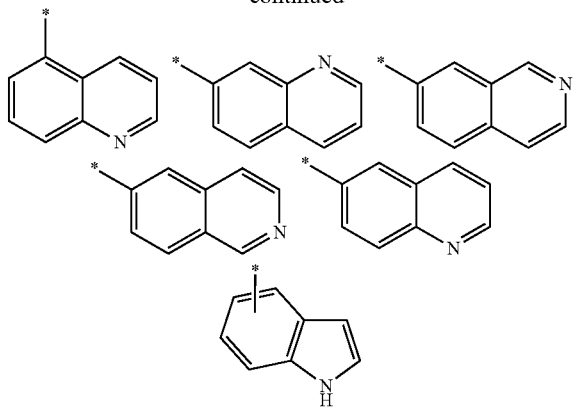

in which -* indicates a bond to the oxygen of Formula 1.

2. The photo-decomposable compound as claimed in claim 1, wherein $Y^a$ is a C1 to C5 substituted or unsubstituted alkylene group, a C5 to C20 divalent monocyclic or condensed alicyclic hydrocarbon group, or a C5 to C20 divalent monocyclic or condensed aromatic hydrocarbon group.

3. The photo-decomposable compound as claimed in claim 1, wherein:

$Y^a$ is —$(CH_2)_m$—, and m is an integer of 1 to 5.

4. The photo-decomposable compound as claimed in claim 1, wherein:

$Y^a$ is one of the following groups:

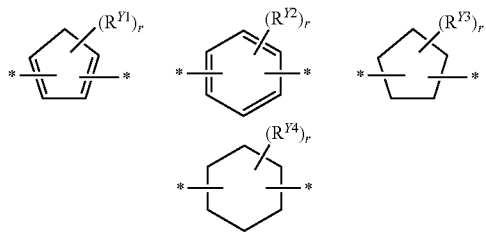

-* is a bond to the carbonyl carbon or the fluorinated carbon of Formula 1, r is an integer of 0 to 2, and each of $R^{Y1}$, $R^{Y2}$, $R^{Y3}$, and $R^{Y4}$ is independently a C1 to C10 linear or branched alkyl group, a cyclopropyl group, a cyclopentyl group, or a cyclohexyl group.

5. The photo-decomposable compound as claimed in claim 1, wherein $A^+$ is a sulfonium cation, an iodonium cation, or an ammonium cation.

6. The photo-decomposable compound as claimed in claim 1, wherein the compound generates acid having an acid dissociation constant of 1 to 10.

7. A photoresist composition, comprising:

a chemically amplified polymer;

a photoacid generator;

a photo-decomposable compound; and a solvent, wherein the photo-decomposable compound is represented by Formula 1:

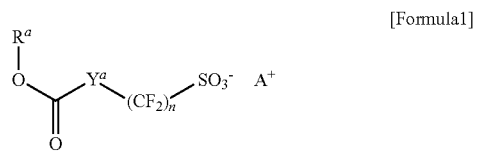

[Formula1]

wherein, in Formula 1, $Y^a$ is a C1 to C20 divalent linear or cyclic hydrocarbon group, n is an integer of 1 to 5, and $A^+$ is a counter ion, $R^a$ is one of the following groups:

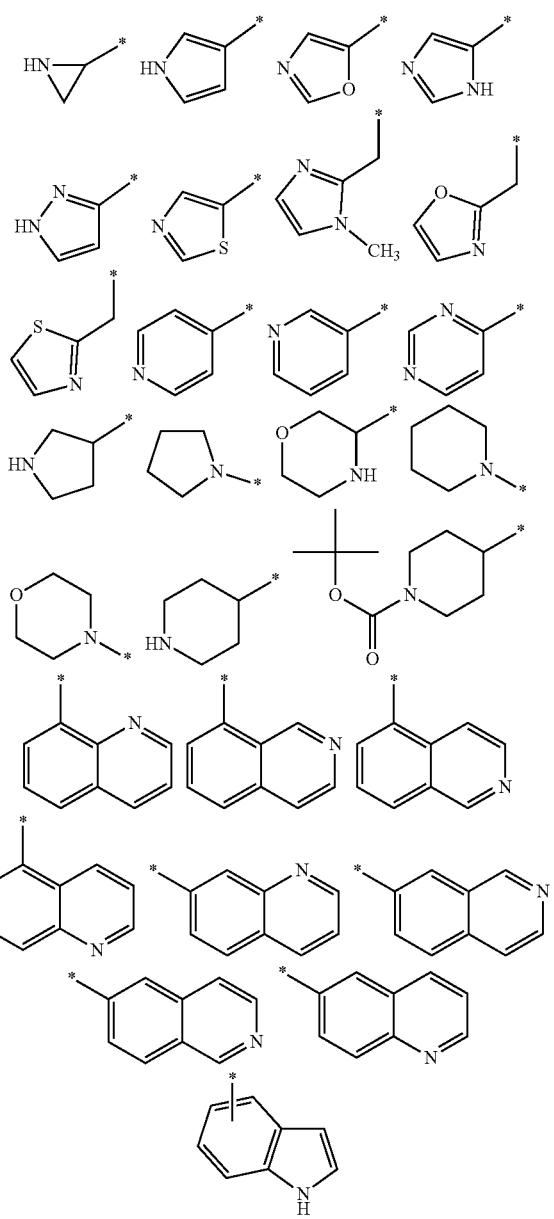

in which -* indicates a bond to the oxygen of Formula 1.

8. The photoresist composition as claimed in claim 7, wherein:
the photoacid generator generates a first acid having a first acid dissociation constant,
the photo-decomposable compound generates a second acid having a second acid dissociation constant, and
the second acid dissociation constant is higher than the first acid dissociation constant.

9. The photoresist composition as claimed in claim 7, wherein:
$Y^a$ is a divalent group represented by —$(CH_2)_m$—, and m is an integer of 1 to 5.

10. A method of manufacturing an integrated circuit device, the method comprising:
providing a substrate that includes a feature layer;
forming a photoresist film on the feature layer, the photoresist film including a chemically amplified polymer, a photoacid generator, and the photo-decomposable compound as claimed in claim 1;
exposing a first area of the photoresist film to generate a first acid and a second acid in the first area of the photoresist film, wherein the first area is a portion of the photoresist film, the first acid is derived from the photoacid generator, and the second acid is derived from the photo-decomposable compound;
deprotecting an acid-labile group included in the chemically amplified polymer by using the first acid and the second acid in the exposed first area of the photoresist film;
removing the exposed first area of the photoresist film by using a developer to form a photoresist pattern comprising a non-exposed area of the photoresist film; and
processing the feature layer using the photoresist pattern.

11. The method as claimed in claim 10, wherein:
forming the photoresist film includes coating the feature layer with a photoresist composition, and
the photoresist composition includes the chemically amplified polymer, the photoacid generator, the photo-decomposable compound, and a solvent.

12. The method as claimed in claim 10, wherein the photo-decomposable compound is represented by Formula 1a, in which $R^a$ is defined the same as that of Formula 1:

[Formula 1a]

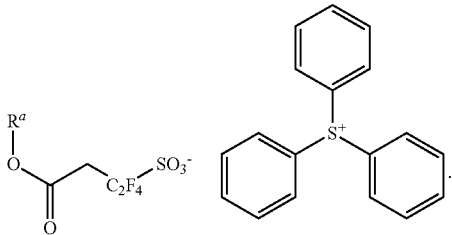

13. The method as claimed in claim 10, wherein:
during the exposing of the first area of the photoresist film, the first acid has a first acid dissociation constant, and the second acid has a second acid dissociation constant, and
the second acid dissociation constant is higher than the first acid dissociation constant.

14. The method as claimed in claim 10, wherein exposing the first area of the photoresist film includes exposing the first area using an extreme ultraviolet laser.

* * * * *